United States Patent [19]

Maegawa et al.

[11] Patent Number: 5,162,570

[45] Date of Patent: Nov. 10, 1992

[54] PROCESS FOR PRODUCING 1,4-DIHYDROXY-2-ARYLNAPHTHOATE

[75] Inventors: Yuzo Maegawa, Osaka; Yasuhiro Nishida, Hyogo, both of Japan

[73] Assignees: Sumitomo Chemical Company, Limited, Osaka; Daiei Chemical Company, Limited, Hyogo, both of Japan

[21] Appl. No.: 542,440

[22] Filed: Jun. 22, 1990

[30] Foreign Application Priority Data

Jun. 27, 1989 [JP] Japan .................................. 1-166006
Jul. 19, 1989 [JP] Japan .................................. 1-187645
Jul. 19, 1989 [JP] Japan .................................. 1-187646

[51] Int. Cl.$^5$ .............................................. C07C 69/76
[52] U.S. Cl. ...................................................... 560/56
[58] Field of Search ............................................ 560/56

[56] References Cited

FOREIGN PATENT DOCUMENTS

| 58-22021 | 5/1983 | Japan . |
| 1-45341 | 2/1989 | Japan . |
| 64-45341 | 2/1989 | Japan . |
| 64-45342 | 2/1989 | Japan . |
| 64-45343 | 2/1989 | Japan . |

OTHER PUBLICATIONS

Chemical Abstracts, vol. 111, Abstract No. 77668, 1989.
Chemical Abstracts, vol. 111, Abstract No. 77669, 1989.
Chemical Abstracts, vol. 111, Abstract No. 77670, 1989.

*Primary Examiner*—Paul J. Killos
*Attorney, Agent, or Firm*—Darby & Darby

[57] ABSTRACT

Pure 1,4-dihydroxy-2-arylnaphthoate is prepared in high yield by allowing 1,4-dihydroxy-2-naphthoic acid to react with triarylphosphite in the presence of an acid catalyst selected from organic and inorganic acids and crystallizing from a mixed solvent consisting essentially of lower alcohols and water until 1,4-dihydroxy-2-naphthoic acid is isolated and is further purified by crystallization from a mixed solvent consisting essentially of lower alcohols, water and extraction solvent, i.e., alkyl-substituted aromatic hydrocarbons or halogen-substituted aliphatic or aromatic hydrocarbons.

12 Claims, No Drawings

PROCESS FOR PRODUCING 1,4-DIHYDROXY-2-ARYLNAPHTHOATE

This invention relates to a process for producing 1,4-dihydroxy-2-arylnaphthoate which is useful as an intermediate for photo-chemicals, dyes and pigments.

Polycyclicoxy-arylcarbonate is prepared by an esterification, i.e. dehydration, of polycyclicoxy-carboxylic acid and phenol. Strong acid, which is usually used as a catalyst for esterifications, is hardly used as a catalyst, because it decomposes the carboxylic acid. Instead, phosphorus trichloride, phosphorus oxychloride, phosphorous pentachloride or the like is used as the catalyst or a dehydrating agent. However, these conventional processes are not satisfactory yet as industrial processes, because they produce colored products. In addition, many difficulties are encountered such as complicated or troublesome after-treatments for removal of phenols from waste water because a large-excess amount of phenols are used as solvents as well as reactants.

In order to solve above mentioned problems, Japanese patent publication No. 83-22021 and Japanese laid open No. 89-45341 disclose a process using triarylphosphite as a reactant. The process, however, has a problem that products of high purity are hardly obtained, because it is accompanied by a considerable amount of by-products such as a dimer of the following formula (Japanese laid open No. 89-45343):

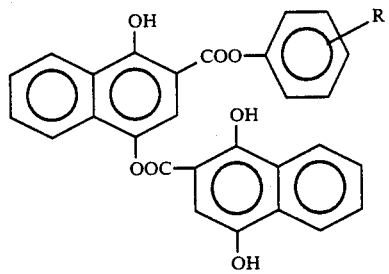

wherein R is a hydrogen, halogen atom or $C_{1-10}$ alkyl.

An object of this invention is to provide a favorable industrial process for preparing 1,4-dihydroxy-2-arylnaphthoate of high purity.

According to the present invention, 1,4-dihydroxy-2-arylnaphthoate of the formula (I)

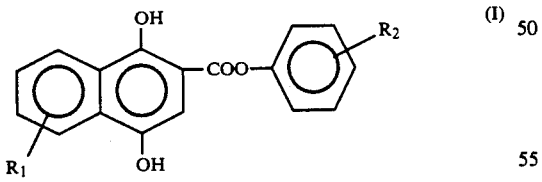

wherein $R_1$ and $R_2$ are the same or different and a hydrogen atom, a lower alkyl group and a halogen atom, is prepared by allowing 1,4-dihydroxy-2-naphthoic acid to react with triarylphosphite in the presence of an acid catalyst selected from organic or inorganic acids (hereinafter this process is referred to as process I).

This invention also provides a process for producing 1,4-dihydroxy-2-arylnaphthoate of the formula (I) above which comprises crystallizing a reaction product containing 1,4-dihydroxy-2-arylnaphthoate as the principle ingredient, which is obtained by allowing 1,4-dihydroxy-2-naphthoic acid to react with triarylphosphite in a mixed solvent consisting essentially of lower alcohol and water (hereinafter this process is referred to as process II).

This invention further provides a purification process for 1,4-dihydroxy-2-arylnaphthoate of the formula (I) which contains dimer of the formula (II) mentioned above as a main by-products,

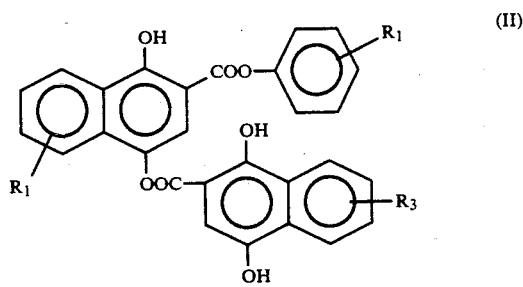

wherein each of $R_1$, $R_2$ and $R_3$ is a hydrogen atom, a lower alkyl group and a halogen atom, individually, which comprises adding water and an extraction solvent selected from a group consisting of alkyl-substituted aromatic hydrocarbons, halogen-substituted aliphatic hydrocarbons and halogen-substituted aromatic hydrocatons to a solution of 1,4-dihydroxy-2-arylnaphthoate containing the dimer in a mixed solvent consisting essentially of alcohol and water until 1,4-dihydroxy-2-arylnaphthoate is crystallized (hereinafter this process is referred to as process III).

Triarylphosphite used in process I is prepared by a known method (Japanese patent publication No. 83-22021, Japanese laid open No. 89-45341). That is, phosphorus trichloride (one mol) is allowed to react with phenols such as phenols, halogenated phenols, and phenols substituted with a $C_{1-20}$ alkyl group (not less than 3 mols) in the presence of an acid catalyst. The acid catalysts include an organic acid such as an aromatic sulfonic acid of the following formula (III) or (IV)

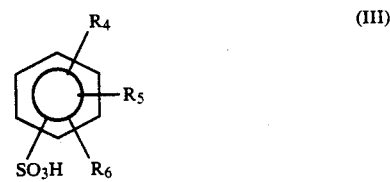

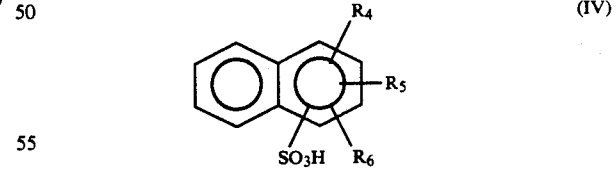

wherein each of $R_4$, $R_5$ or $R_6$ is individually a hydrogen atom, a $C_{1-10}$ alkyl group, a halogen atom, a nitro group, a sulfonic acid group, a carboxylic group, a hydroxy group or an alkoxy group, or a $C_{1-10}$ aliphatic sulfonic acid such as methane sulfonic acid or ethane sulfonic acid; an inorganic acid such as sulfuric acid or nitric acid; and a Lewis acid such as anhydrous aluminum chloride, anhydrous zinc chloride, iron chloride, tin chloride, boron trifluoride or the like.

Examples of the aromatic sulfonic acid of the formula (III) or (IV) are benzene sulfonic acid; alkyl ($C_{1-10}$)-substituted benzene sulfonic acid, alkyl($C_{1-10}$)-substituted benzene disulfonic acid such as toluene sulfonic acid and xylene sulfonic acid; naphthalene sulfonic acid; alkyl($C_{1-10}$)-substituted naphthalene sulfonic acid; and alkyl($C_{1-10}$)-substituted naphthalene disulfonic acid. Among them, p-toluene sulfonic acid and chloronitrobenzene sulfonic acid are preferred.

An amount of triarylphosphite used as a reactant in the process I is 0.9–3.5 mol, preferably 1.5–3.0 mol, per mol of 1,4-dihydroxy-2-naphthoic acid. An amount of the catalyst used in the process I is 0.01–0.5 mol per mol of 1,4-dihydroxy-2-naphthoic acid, preferably 0.05–0.3 mol.

Reaction temperature of the process I is up to 90° C., preferably 40°–85° C.

The process I is conducted in the absence or presence of a solvent, preferably absence of a solvent. The solvent includes aromatic hydrocarbons such as phenols, cresols, toluene, xylene and the like; halogenated hydrocarbons such as chlorobenzene; and ketones such as methyl-n-propyl ketones, methyl-n-butyl ketone, methyl-isobutyl ketone, diisobutyl ketone and the like.

1,4-Dihdyroxy-2-arylnaphthoate is isolated according to a known process. The process II, if applied to, is convenient, since the compound is obtained in a shorter period of time with high purity.

According to process I, an amount of by-products is so small that 1,4-dihydroxy-2-arylnaphthoate is obtained with high purity in high yield. Accordingly, process I is a very economical process.

The process II may preferably be applied to the reaction product obtained by the process I but also to a reaction product of 1,4-dihydroxy-2-arylnaphthoic acid with triarylphosphite obtained by a process such as mentioned in Japanese patent publication No. 83-22021 and Japanese laid open No. 89-45341.

The lower alcohol used in the process II is $C_{1-4}$ aliphatic alcohol such as methanol, ethanol, n-propyl alcohol, isopropyl alcohol, n-butyl alcohol or the like. Among them, methanol is preferable. An amount of the lower alcohol in the mixed solvent used in the process II is 5–50 parts by volume every 100 parts by volume of the mixed solvent, preferably 10–30 parts. An amount of the mixed solvent used in the process II is 1–10 parts by weight per part by weight of the reaction product used in the process II, preferably 2–8 parts.

Crystallization of the reaction product from the mixed solvent is conducted at a temperature of 0°–80° C., preferably 20°–55° C.

The crystallization process in the process II is usually conducted by discharging and diluting the reaction product into the mixed solution, and then, if necessary, heating and/or cooling, under stirring, until the product is crystallized. The crystallized product thus obtained is subjected to an after-treatment such as filtration, washing, drying or the like according to known methods.

According to the process II, not only the time for crystallizing the reaction product and the time for the filtration are made shorter, but also highly pure 1,4-dihydroxy-2-arylnaphthoate is isolated, in high yield.

Accordingly, the process II is very economical, too.

1,4-Dihydroxy-2-arylnaphthoate thus obtained may often contain the dimer of formula (II) as an impurity. The process III is applied to in order to remove the dimer.

The process III is applied not only to the product obtained by the processes I and II, but also to 1,4-dihydroxy-2-arylnaphthoate containing the dimer of the formula (II) as the main by-product. For instance, the process III is applied to a reaction product produced according to a process using triarylphosphite as a reactant such as process I or a process mentioned in Japanese patent publication No. 83-22021 or Japanese laid open No. 89-45341.

In the process III, an amount of the alcohol is 2.0–20.0, preferably 30–10.0 more preferably 5.0–7.0 parts by weight per part by weight of 1,4-dihydroxy-2-arylnaphthoate. Initially, an amount of the water in the mixed solvent is preferably 0.5–10 aprts every 100 parts of the alcohol.

Water and an extraction solvent are added to a solution of 1,4-dihydroxy-2-arylnaphthoate in the mixed solvent. Preferably, the extraction solvent is added first before water is added. An amount of the water to be added is so determined that alcohol content in the following formula is 20–60%, preferably 25–50%.

Alcohol content = volume of alcohol/(volume of alcohol + volume of total water) × 100 (%)

An amount of the extraction solvent in the mixed solvent is 0.3–3.0, preferably 0.5–2.5 parts by weight per part by weight of 1,4-dihydroxy-2-arylnaphthoate.

Examples of the alcohol used in process III are methanol, ethanol and the like, preferably methanol. The extraction solvent includes alkyl-substituted hydrocarbons such as toluene, xylene, ethylbenzene and the like; halogenated aliphatic hydrocarbons such as dichloromethane; and halogenated aromatic hydrocarbons such as monochlorobenzene and dichlorobenzne.

According to the process III, 1,4-dihydroxy-2-arylnaphthoate containing a greatly small amount of by-product is obtained. The process III is very favorable from an industrial point of view.

This invention is explained in more detail by the following Examples, but it is not limited thereto.

EXAMPLE 1

Into a reactor (one liter) equipped with a stirrer, were charged 241 g of triphenylphosphite (hereinafter referred to as TPP), 59.5 g of 1,4-dihydroxy-2-naphthoic acid (hereinafter referred to as AOH), and 6.6 g of p-toluenesulfonic acid (hereinafter referred to as PTS). The mixture was heated until temperature reached 80° C. and kept at 80° C. for 5 hours in order to complete the reaction. The reaction product was brownish transparent liquid. Completion of the reaction was determined by amount of unaltered AOH which was measured by liquid chromatography during the reaction.

EXAMPLE 2

The reaction product obtained in Example 1 was poured dropwise into 1200 g of a methanol/water mixed solvent in which weight percentage of methanol was 16.7%. The mixture was stirred at 50° C. for 3 hours, and then cooled until crystals were precipitated. The crystallized product was filtrated, washed with water to obtain 100 g of crude 1,4-dihydroxy-2-phenylnaphthoate (hereinafter referred to as crude ONH). Using a very small amount of crude ONH obtained, a solid content was measured, and a composition of the crude ONH was analized by liquid chromatography, to give the results that solid: 80 g in 100 g of the crude ONH,
composition of the solid: pure 1,4-dihydroxy-2-phenylnaphthoate 92.5% by weight 4-(1',4'-dihydroxy-2'-naphthoyl)-oxy-1-hydroxy-2-phenylnaphthoate (one of the dimers of the formula II, hereinafter referred to as DNO): about 7.5%.

EXAMPLE 3

Into a reactor (one liter) equipped with a stirrer, was charged about 100 g of the crude ONH obtained in Example 1, 528 g of methanol and 6.4 g of water. The mixture was heated until temperature reached 50° C. and kept at 50° C. for 30 minutes. The mixture was filtrated while the solution was warm and 88 g of toluene was added to the filtrate. The solution obtained was stirred at 30°-40° C. for 10 minutes, and diluted with water to control weight percentage of methanol (=(weight of methanol)×100/(weight of methanol and water)) to 40% until 1,4-dihydroxy-2-phenylnaphthoate was crystallized. The crysal (hereinafter referred to as ONH) was filtrated, washed witn 200 g of 40% methanol in water and dried to obtain 64 g of ONH. Analysis by liquid chromatography showed that the ONH contains 1,4-dihydroxy-2-phenylnaphthoate (99.6%) and DNO (0.4%).

EXAMPLE 4

Examples 1 and 2 were repeated except that an amount of the TPP was changed to 171.8 g, and 79.5 g of crude ONH was obtained. Composition of the crude ONH obtained was analyzed by liquid chromatography. The results are shown in Table 1.

EXAMPLE 5

Examples 1 and 2 were repeated except that 6.0 g of benzene sulfonic acid was used in place of the PTS (6.6 g) and 79.5 g of crude ONH was obtained. Composition of the crude ONH obtained was analyzed by liquid chromatography. The results are shown in Table 1.

EXAMPLE 6

Into a reactor (one liter) equipped with a stirrer, were charged 241 g of TPP, 59.6 g of AOH and 3.7 g of methanesulfonic acid. The reaction and isolation were carried out in the same manner as in Examples 1 and 2 to obtain 77 g of crude ONH. Composition of crude ONH obtained was analyzed by liquid chromatography. The results are shown in Table 1.

EXAMPLE 7

Into a reactor (one liter) equipped with a stirrer, were charged 241 g of TPP, 59.6 g of AOH, 6 g of PTS and 130 ml of methylisobutylketone. The reaction was carried out in the same manner as in Example 1. After completion of the reaction was confirmed, methylisobutylketone was distilled off under reduced pressure and isolation of the reaction product was carried out in the same manner as in Example 2 to obtain 75.0 g of crude ONH. Composition of crude ONH obtained was analyzed by liquid chromatography. The results are shown in Table 1.

EXAMPLE 8

Into a reactor (one liter) equipped with a stirrer, were charged 241 g of TPP, 59.6 g of AOH and 9.0 g of 3-nitro-4-chlorobenzene sulfonic acid. The mixture was heated until temperature reached 50° C., and kept at 50° C. for 5 hours to complete the reaction. The reaction product was brownish transparent liquid. Completion of the reaction was determined by an amount of unaltered AOH measured by liquid chromatography.

EXAMPLE 9

The reaction product obtained in Example 8 was poured dropwise into 1200 g of methanol/water mixed solvent (50° C.) in which weight percentage of methanol is 16.7%. The mixture was stirred at 50° C. for 3 hours, and then cooled to the room temperature until crystals were obtained. Then, the crysallized product was filtrated and washed with water to obtain 100 g of crude ONH. Solid content and composition of the crude ONH was analyzed in the same manner as in Example 2. The results are:
  solid: 80 g in 100 g of crude ONH composition of the solid: pure 1,4-dihydroxy-2-phenylnaphthoate 94.5% by weight
  DNO: about 5.5% by weight.

EXAMPLE 10

Into a reactor (one liter) equipped with a stirrer, were charged 241 g of TPP, 63.6 g of 1,4-dihydroxy-7-methyl-2-naphthoic acid (hereinafter referred to as methyl AOH), and 6.6 g of PTS. The mixture was heated until temperature reached 80° C., and kept at 80° C. for 5 hours in order to complete the reaction. The reaction product was brownish transparent liquid. Completion of the reaction was determined by an amount of unaltered methyl AOH measured by liquid chromatography.

EXAMPLE 11

The reaction product obtained in Example 10 was poured dropwise into 1200 g of a methanol/water mixed solvent (80° C.) in which weight percentage of methanol is 16.7%. The mixture was stirred at 50° C. for 3 hours, and then cooled to room temperature until crystals were precipitated. Then the crystallized product was filtrated, washed with water, and dried to obtain 82.3 g of crude product (hereinafter referred to as crude methyl-ONH).

Analysis of the crude methyl-ONH gave the resutls that the crude methyl-ONH contains 92.0% of pure 1,4-dihydroxy-7-methyl-2-phenylnaphthoate.

COMPARATIVE EXAMPLE 1

Into a reactor (one liter) equipped with a stirrer, were charged 59.6 g of AOH and 241 g of TPP. Reaction and isolation were carried out in the same manner as in Examples 1 and 2 to obtain 61 g of crude ONH. The results of analysis of the crude ONH by liquid chromatography are shown in Table 1.

COMPARATIVE EXAMPLE 2

Into a reactor (one liter) equipped with a stirrer, were charged 59.6 g of AOH and 181.3 g of TPP. The mixture was heated up to 110° C. and kept at 110° C. for 10 hours. Then the reaction products was cooled to 50° C., mixed with 300 ml of water, cooled and kept at room temperature for 5 hours in order to crystallize the product. The cristayllized product was filtrated, washed with water and dried to obtain 72 g of crude ONH. The results of analysis of the crude ONH by liquid chromatography are shown in Table 1.

TABLE 1

| | Composition % by weight | |
| --- | --- | --- |
| | 1,4-dihydroxy-2-phenylnaphthoate | by-product (mainly DNO) |
| Example 4 | 90.0 | 10.0 |

TABLE 1-continued

| | Composition % by weight | |
|---|---|---|
| | 1,4-dihydroxy-2-phenylnaphthoate | by-product (mainly DNO) |
| Example 5 | 91.0 | 9.0 |
| Example 6 | 88.0 | 12.0 |
| Example 7 | 91.5 | 8.5 |
| Comparative Example 1 | 55.0 | 25.4 (also contains 23.0% of unaltered AOH) |
| Comparative Example 2 | 65.5 | 34.5 |

EXAMPLE 12

Example 1 was repeated and completion of the reaction was confirmed. The reaction product obtained was poured dropwise into 1200 g of an ethanol/water mixed solvent in which weight percentage of ethanol was 16.7%. Isolation of the product was carried out in the same manner as in Example 2 to obtain 78 g of crude ONH.

EXAMPLE 13

Example 1 was repeated and completion of the reaction was confirmed. The reaction product obtained was poured dropwise into 1200 g of an isopropyl alcohol/water mixed solvent in which weight percentage of isopropyl alcohol was 16.7%. Isolation of the product was carried out in the same manner as in Example 2 to obtain 79 g of crude ONH.

EXAMPLE 14

Example 1 was repeated and completion of the reaction was confirmed. The reaction product obtained was poured dropwise into 750 g of a methanol/water mixed solvent in which weight percentage of methanol was 25%. Isolation of the product was carried out in the same manner as in Example 2 to obtain 77 g of crude ONH.

EXAMPLE 15

Example 1 was repeated and completion of the reaction was confirmed. The reaction product obtained was poured dropwise into 1600 g of a methanol/water mixed solvent in which weight percentage of methanol was 5%. Isolation of the product was carried out in the same manner as in Example 2 to obtain 80 g of crude ONH.

COMPARATIVE EXAMPLE 3

Example 1 was repeated and completion of the reaction was confirmed. The reaction product obtained was poured into 1200 g of water and stirred at 50° C. for 10 hours. The reaction product was not dispersed well in the water until a dumpling-like solid was formed. After removing the aqueous solution by decantation, 1200 g of warm water was added again and stirring was made at 50° C. for 5 hours to obtain a crystalline product. The crystalline product was filtered, washed and dried to obtain 79 g of crude ONH. Analysis of the crude ONH by liquid chromatography gave the results that the crude ONH obtained contains 90.5% of pure 1,4-dinhdroxy-2-phenylnaphthoate and 8.5% of DNO.

EXAMPLE 16

Examples 1 and 2 were repeated to botain crude ONH to which 400 g of methanol was added until a solution was obtained. The solution was heated until temperature reached 50° C. and filtrated to remove insoluble matters. Toluene (50 g) was added to the filtrate. The solution obtained was stirred at 30°–40° C. for 10 minutes, and diluted with water in order to control weight percentage of the methanol (=(weight of methanol)×100/(weight of methanol and water)) to 30% and crystallize ONH. The crystallized ONH was filtrated, washed with 30% methanol/water and dried to obtain 67 g of ONH. Analysis by liquid chromatography shows that the ONH contains 1,4-dihydroxy-2-phenylnaphthoate (99.0%) and DNO (1.0%).

EXAMPLE 17

Examples 1, 2 and 3 were repeated excpet that 88 g of xylene was used in place of the toluene to obtain 63 g of ONH. Analysis of the ONH by liquid chromatography shows that the ONH contains 1,4-dihydroxy-2-phenylnaphthoate (99.1%) and DNO (0.9%).

COMPARATIVE EXAMPLE 4

Examples 1 and 2 were repeated to obtain crude ONH. Into a reactor (one liter) equipped with a stirrer, were charged 100 g of the crude ONH obtained, 528 g of methanol, and 6.4 g of water. The mixture was heated until temperature reached 50° C. and kept at 50° C. for 30 minutes. The mixture was filtrated while the solution was still warm to obtain filtrate. The solution, i.e. the filtrate obtained was diluted with water in order to control weight percentage of methanol (=(weight of methanol)×100/(weight of methanol and water)) to 40% and to crystallize 1,4-dihydroxy-2-phenylnaphthoate. The crystallized ONH was filtrated, washed with 200 g of 40% methanol/water and dried to obtain 66 g of ONH. Analysis of the ONH by liquid chromatography shows that the ONH contains 1,4-dihydroxy-2-phenylnaphthoate (95.5%) and DNO (4.5%).

What we claim is:

1. A process for producing 1,4-dihydroxy-2-arylnaphthoate of the formula (I)

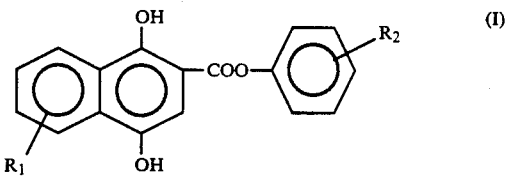

wherein $R_1$ and $R_2$ are the same or different and selected from a hydrogen atom, a lower alkyl group and a halogen atom, which comprises allowing 1,4-dihydroxy-2-naphtoic acid to react with triarylphosphite in the presence of an acid wherein said catalyst is not said 1,4-dihydroxy-2-naphthoic acid catalyst selected from organic and inorganic acids.

2. A process for producing 1,4-dihydroxy-2-arylnaphthoate of the formula (I)

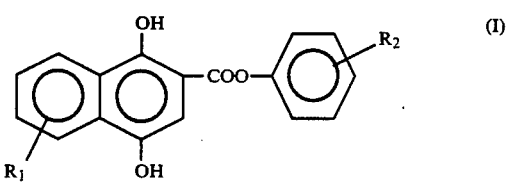

wherein $R_1$ and $R_2$ are the same or different and selected from a hydrogen atom, a lower alkyl group and a halogen atom, which process comprises allowing 1,4-dihydroxy-2-naphthoic acid to react with triarylphosphite in the presence of an acid catalyst, wherein the acid catalyst is an aromatic sulfonic acid of the following formula (III) or (IV)

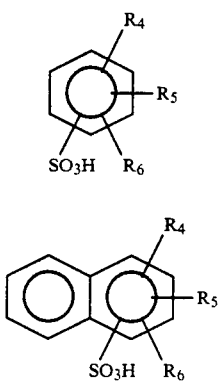

, wherein each of $R_4$, $R_5$ $R_6$ is individually a hydrogen atom, a $C_{1-10}$ alkyl group, a halogen atom, a nitro group, a sulfonic acid group, a carboxylic group, a hydroxy group, an alkoxy group or a $C_{1-10}$ alphatic sulfonic acid.

3. The process according to claim 2, wherein the acid catalyst is p-toluene sulfonic acid or chloronitrobenzene sulfonic acid.

4. The process according to claim 2, wherein an amount of triarylphosphite is 0.9-3.5 mol per mol of 1,4-dihydroxy-2-naphthoic acid.

5. The process according to claim 2, wherein an amount of acid catalyst is 0.01-0.5 mol per mol of 1,4-dihydroxy-2-naphthoic acid.

6. The process according to claim 2, wherein reaction temperature is 40° to 85° C.

7. The process for producing 1,4-dihydroxy-2-arylnaphthoate of the formula (I) according to claim 2 further comprising crystallizing the reaction product in a mixed solvent which consists essentially of lower alcohols and water.

8. The process according to claim 7, wherein an amount of the lower alcohols in the mixed solvent is 5 to 50 parts by volume every 100 parts by volume of the mixed solvent.

9. The process according to claim 8, wherein an amount of the mixed solvent is 1 to 10 parts by weight per part by weight of the reaction product.

10. The process according to claim 7, wherein the lower alcohols are $C_{1-4}$ aliphatic alcohols.

11. The process according to claim 7, wherein the lower alcohol is methanol.

12. The process according to claim 7, wherein crystallizing the reaction product is conducted at a temperature of 20° to 55° C.

* * * * *

UNITED STATES PATENT AND TRADEMARK OFFICE
CERTIFICATE OF CORRECTION

PATENT NO. : 5,162,570
DATED : November 10, 1992
INVENTOR(S) : Yuzo Maegawa, et. al.

It is certified that error appears in the above-indentified patent and that said Letters Patent is hereby corrected as shown below:

Title page, item [73], Assignee: should read --Sumika Fine Chemical co., Ltd., Osaka--.

Signed and Sealed this

Twenty-fourth Day of January, 1995

Attest:

BRUCE LEHMAN

Attesting Officer

*Commissioner of Patents and Trademarks*

UNITED STATES PATENT AND TRADEMARK OFFICE
CERTIFICATE OF CORRECTION

PATENT NO. : 5,162,570
DATED : November 10, 1992
INVENTOR(S) : Yuzo Maegawa, et. al.

It is certified that error appears in the above-indentified patent and that said Letters Patent is hereby corrected as shown below:

Title page, item [73], Assignee: should read --Sumika Fine Chemical co., Ltd., Osaka--.

Signed and Sealed this

Twenty-first Day of February, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,162,570
DATED : November 10, 1992
INVENTOR(S) : Yuzo Maegawa et al It is certified that error appears in the above-indentified patent and that said Letters Patent is hereby corrected as shown below:

title page: [73] Assignees: should read --Sumitomo Chemical Company, Limited and Sumika Fine Chemical Co., Ltd., both of Osaka, Japan--.

This certificate supersedes Certificate of Correction issued January 24, 1995 and February 21, 1995.

Signed and Sealed this

Fifth Day of September, 1995

Attest:

BRUCE LEHMAN

*Attesting Officer*      *Commissioner of Patents and Trademarks*